United States Patent
Federspiel et al.

(10) Patent No.: US 9,814,821 B2
(45) Date of Patent: Nov. 14, 2017

(54) DEVICES, SYSTEMS AND METHODS FOR REDUCING THE CONCENTRATION OF CARBON DIOXIDE IN BLOOD

(71) Applicant: University of Pittsburgh—Of The Commonwealth System of Higher Education, Pittsburgh, PA (US)

(72) Inventors: William J. Federspiel, Pittsburgh, PA (US); David T. Arazawa, Pittsburgh, PA (US); Jeremy D. Kimmel, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 338 days.

(21) Appl. No.: 14/405,038

(22) PCT Filed: Jun. 15, 2013

(86) PCT No.: PCT/US2013/046042
§ 371 (c)(1),
(2) Date: Dec. 2, 2014

(87) PCT Pub. No.: WO2013/188861
PCT Pub. Date: Dec. 19, 2013

(65) Prior Publication Data
US 2015/0129493 A1 May 14, 2015

Related U.S. Application Data

(60) Provisional application No. 61/660,013, filed on Jun. 15, 2012.

(51) Int. Cl.
*B01D 11/00* (2006.01)
*B01D 63/00* (2006.01)
(Continued)

(52) U.S. Cl.
CPC ............ *A61M 1/34* (2013.01); *A61M 1/1698* (2013.01); *B01D 61/00* (2013.01); *B01D 63/02* (2013.01);
(Continued)

(58) Field of Classification Search
CPC ...... B01D 53/22; B01D 53/228; B01D 63/02; B01D 69/02; B01D 69/08; B01D 71/70; B01D 2311/2653; B01D 2257/504
See application file for complete search history.

(56) References Cited

U.S. PATENT DOCUMENTS 4,268,279 A * 5/1981 Shindo ................ B01D 53/228
210/321.8
5,902,747 A 5/1999 Nemser
(Continued)

FOREIGN PATENT DOCUMENTS

DE 4028311 12/1991
WO WO2007146162 A2 12/2007
(Continued)

OTHER PUBLICATIONS

Federspiel, W.J. et al., Lung, Artificial: Basic principles and current applications; 2004; Encyclo Biomat Biomed Eng 910-921.
(Continued)

*Primary Examiner* — Ana Fortuna
(74) *Attorney, Agent, or Firm* — Bartony & Associates, LLC (57) ABSTRACT

A method for removal of at least a portion of carbon dioxide from an aqueous fluid such as a blood fluid includes placing a first surface of at least one membrane through which carbon dioxide and at least one acid gas other than carbon dioxide can pass in fluid in contact with the fluid. The membrane limits or prevent passage of the fluid therethrough. A carrier or sweep gas including the acid gas other
(Continued)

than carbon dioxide is passed over a second surface (which is typically opposite the first surface) of the membrane so that the acid gas other than carbon dioxide can pass through the membrane into the fluid, and carbon dioxide from the fluid can pass from the liquid, through the membrane, and into the sweep gas.

29 Claims, 7 Drawing Sheets (51) Int. Cl.
| | |
|---|---|
| B01D 53/22 | (2006.01) |
| B01D 71/70 | (2006.01) |
| A61M 1/34 | (2006.01) |
| A61M 1/16 | (2006.01) |
| B01D 61/00 | (2006.01) |
| B01D 63/02 | (2006.01) |
| B01D 67/00 | (2006.01) |
| B01D 69/14 | (2006.01) |
| B01D 71/26 | (2006.01) |
| B01D 63/04 | (2006.01) |
| B01D 69/08 | (2006.01) |
| A61M 1/36 | (2006.01) |

(52) U.S. Cl.
CPC ......... *B01D 63/04* (2013.01); *B01D 67/0093* (2013.01); *B01D 69/08* (2013.01); *B01D 69/144* (2013.01); *B01D 71/26* (2013.01); *A61M 1/3687* (2013.01); *A61M 2202/0225* (2013.01); *A61M 2202/0275* (2013.01); *A61M 2202/0283* (2013.01); *B01D 2311/13* (2013.01)

(56) References Cited

U.S. PATENT DOCUMENTS

| | | | | |
|---|---|---|---|---|
| 5,907,747 | A * | 5/1999 | Diener | G03G 15/0894 222/DIG. 1 |
| 7,763,097 | B2 * | 7/2010 | Federspiel | A61M 1/1698 210/500.21 |
| 7,909,788 | B2 | 3/2011 | Monzyk | |
| 8,043,411 | B2 | 10/2011 | Federspiel | |
| 8,252,094 | B2 * | 8/2012 | Ziembinski | A61M 1/1698 264/45.9 |
| 8,569,052 | B2 * | 10/2013 | Federspiel | A01N 1/0236 435/283.1 |
| 9,294,990 | B2 * | 3/2016 | Lee | H04W 48/16 |
| 2003/0133835 | A1 | 7/2003 | Hattler | |
| 2006/0162554 | A1 * | 7/2006 | Kelley | B01D 53/22 95/45 |
| 2010/0198132 | A1 | 8/2010 | Pesenti | |
| 2010/0300114 | A1 * | 12/2010 | Mhadeshwar | B01D 53/22 60/783 |
| 2010/0331767 | A1 | 12/2010 | Frankowski | |
| 2011/0174156 | A1 * | 7/2011 | Saunders | B01D 53/1475 95/46 |
| 2012/0040429 | A1 * | 2/2012 | Federspiel | A61M 1/1698 435/180 |

FOREIGN PATENT DOCUMENTS

| | | |
|---|---|---|
| WO | WO2008135282 A2 | 11/2008 |
| WO | WO2013188861 | 12/2013 |

OTHER PUBLICATIONS

Zanella, A., et al.; Blood Acidification Enhances Carbon Dioxide Removal of Membrane Lung: An Experimental Study, Intensive Care Medicine 35, No. 8 (2009): 1484-1487.

Snider, M. T., et al. Augmentation of CO2 Transfer in Membrane Lungs by the Infusion of a Metabolizable Organic Acid. ASAIO Journal 33, (1987).

Zanella, A., et al. Infusion of 2.5 meq/min of lactic acid minimally increases CO2 production compared to an isocaloric glucose infusion in healthy anesthetized, mechanically ventilated pigs. Critical Care 17, R268 (2013).

Zanella, A., et al. Regional Blood Acidification Enhances Extracorporeal Carbon Dioxide Removal: A 48-hour Animal Study. Anesthesiology 120, 416-424 (2014).

Zanella, A., et al. Extracorporeal carbon dioxide removal through ventilation of acidified dialysate: An experimental study. The Journal of Heart and Lung Transplantation, 2013.12.006.

* cited by examiner

DEVICES, SYSTEMS AND METHODS FOR REDUCING THE CONCENTRATION OF CARBON DIOXIDE IN BLOOD

CROSS-REFERENCE TO RELATED APPLICATION

This application claims benefit of U.S. Provisional Patent Application No. 61/660,013, filed Jun. 15, 2012, the disclosure of which is incorporated herein by reference.

GOVERNMENTAL INTEREST

This invention was made with government support under grant no. HL70051 awarded by the National Institute of Health: National Heart, Lung, and Blood Institute. The government has certain rights in this invention.

BACKGROUND

The following information is provided to assist the reader to understand the devices, systems, methods and other technology disclosed below and the environment in which they will typically be used. The terms used herein are not intended to be limited to any particular narrow interpretation unless clearly stated otherwise in this document. References set forth herein may facilitate understanding of the devices, systems methods and other technology disclosed below or the background thereof. The disclosure of all references cited herein are incorporated by reference.

In cases of respiratory failure, carbon dioxide ($CO_2$) removal, rather than oxygen ($O_2$) delivery, is often a primary obstacle in treatment. The therapeutic potential of extracorporeal carbon dioxide removal ($ECCO_2R$) in facilitating lung protective ventilation strategies has been established through partial $ECCO_2R$ devices such as the NOVALUNG® interventional lung assist device (a membrane ventilator/extracorporeal artificial lung) available from Novalung GmbH of Heilbronn, Germany and the HEMOLUNG® respiratory assist system (a respiratory assist system/extracorporeal artificial lung) available from ALung Technologies of Pittsburgh, Pa. USA. Such devices, sometimes referred to as artificial lungs, are employed to oxygenate the blood and to remove $CO_2$. Hollow fiber membrane (HFM) based artificial lungs began to replace bubble oxygenators in the 1980s. In that regard, HFM-based artificial lungs exhibit improved gas exchange performance as compared to bubble oxygenators. The first HFM type artificial lung was developed in 1971. However, the performance of early oxygenators was unacceptable as a result of fiber wetting and plasma leak problems.

Composite fibers, constructed with a true membrane layer between microporous walls, are commercially available. Although, the composite fiber had excellent plasma wetting resistance, the permeance of the membrane was insufficient for intravenous oxygenation. Recent advances in membrane technology, however, have enabled the development of noble membranes such as polyolefin-based hollow fiber membrane that exhibit both good gas permeance and high plasma wetting resistance.

Currently available artificial lungs devices typically include bundles of microporous hollow fiber membranes through which oxygen passes while blood is perfused around the fibers. A review of artificial lungs and hollow fiber membrane technology is provided in Federspiel W J, Henchir K A. 2004. Lung, Artificial: Basic principles and current applications. *Encyclo Biomat Biomed Eng* 910-921, the disclosure of which is incorporated herein by reference. In general, oxygen is transferred from the lumen of the fibers into the blood; while $CO_2$ is transferred from the blood into the lumen of the fibers and is removed from the device. In the current artificial lung model, which is based on passive diffusion, the efficiency of $CO_2$ and $O_2$ gas exchange are limited by the fiber surface area to blood volume ratio. Gas exchange can be improved by increasing this ratio at the cost of increasing the overall size of the artificial lung device. Additionally, $CO_2$ removal rates are limited at lower blood flow rates.

SUMMARY

In one aspect, a method for removal of at least a portion of carbon dioxide from an aqueous fluid includes placing a first surface of at least one membrane through which carbon dioxide and at least one acid gas other than carbon dioxide can pass in fluid in contact with the fluid. The membrane limits or prevent passage of the fluid/liquid therethrough. A carrier or sweep gas including the acid gas other than carbon dioxide is passed over a second surface (which is typically opposite the first surface) of the membrane so that the acid gas other than carbon dioxide can pass through the membrane into the fluid, and carbon dioxide from the fluid can pass from the liquid fluid, through the membrane, and into the sweep gas.

In a number of embodiments, the fluid is a blood fluid. The term "blood fluid" as used herein includes whole blood or blood, a component of blood, mixtures of blood components, as well as blood, a blood component, or a mixture of blood components which has been treated and/or altered in any manner (for example, via addition of one or more non-blood components).

In a number of embodiments, the acid gas is biocompatible. As used herein, the term "biocompatible" refers generally to compatibility with living tissue or a living system. The acid gas and/or any byproducts therefrom may, for example, be naturally occurring and/or metabolizable in the body. Acid gasses are further selected for their ability to liberate a $H^+$ proton upon dissolution into an aqueous environment. Examples of suitable acid gases include sulfur dioxide ($SO_2$), hydrogen sulfide ($H_2S$), nitrogen dioxide ($NO_2$), nitric oxide (NO), hydrogen iodide (HI), hydrogen chloride (HCl), hydrogen fluoride (HF), and/or hydrogen bromide (HBr). In the case of, for example, $SO_2$, byproducts, including sulfurous acid, bisulfite and sulfite, are naturally occurring and metabolized in the body. In a number of representative studies hereof, $SO_2$ was used as an acid gas in a sweep gas. While bisulfite and other acid gas products are naturally occurring, such products and/or other products or byproducts may be toxic if introduced above a certain concentration. In some case, a system such as a dialysis or other removal/separation system may be used to remove acid products from a blood fluid before the blood fluid is returned to the body.

In a number of embodiments, the membrane includes immobilized carbonic anhydrase on or in the vicinity of the first surface thereof such that the immobilized carbonic anhydrase comes into contact with the fluid. The first surface may, for example, exhibit carbonic anhydrase activity of at least 20%, 40%, 60%, 80% or 100% of maximum theoretical activity of the first surface of the membrane based on monolayer surface coverage of carbonic anhydrase in the case that the carbonic anhydrase is immobilize on the first surface. In a number of embodiments, the first surface exhibits carbonic anhydrase activity which exceeds the maximum theoretical activity of the first surface of the membrane based on monolayer surface coverage of carbonic anhydrase.

Carbonic anhydrase may, for example, be immobilized on the membrane via adsorption, covalent bonding, ionic bonding or chelation. In a number of embodiments, carbonic anhydrase is covalently attached to the membrane.

The membrane may, for example, include a polymeric material. The polymeric material may, for example, be microporous or permeable such that $CO_2$ and the at least one acid gas other than $CO_2$ can pass therethrough. In a number of embodiments, the polymeric material is microporous and sufficiently hydrophobic so that its pores remain gas filled after contacting blood or other aqueous fluids. In a number of embodiments, the polymeric material is an olefinic polymeric material.

In a number of embodiments, carbonic anhydrase is covalently attached to a first surface of a microporous polymeric hollow fiber. The first surface may, for example, be an outer surface of the hollow fiber. An interior lumen of the hollow fiber may, for example, be adapted to have oxygen flow therethrough. The sweep gas may, for example, further include oxygen. The hollow fiber may, for example, be adapted to pass oxygen and the at least one acid gas other than carbon dioxide into the blood fluid while carbon dioxide passes from the blood fluid to the interior lumen of the hollow fiber. In a number of embodiments, carbonic anhydrase is covalently attached to a permeable, nonporous polymeric layer on an exterior surface of a microporous polymeric hollow fiber. A plurality of membranes formed by a plurality of hollow fibers may, for example, be placed in contact with the fluid. The permeable, nonporous polymeric layer may, for example, include $CO_2$-permeable silicone.

In a number of embodiments, the membrane includes a porous layer and a gas permeable, nonporous layer adjacent the porous layer.

The method may, for example, further include contacting the blood fluid with free carbonic anhydrase. Carbon dioxide may, for example, be present in the fluid in the form of bicarbonate ion.

In another aspect, a device or a system hereof for removal of at least a portion of carbon dioxide from an aqueous fluid, includes at least one membrane including a first surface and a second surface. The membrane is adapted to pass carbon dioxide and at least one acid gas other than carbon dioxide therethrough. The membrane is further adapted to limit or prevent passage of the fluid therethrough. The device and/or system further includes a sweep gas including the acid gas other than carbon dioxide. The sweep gas is passed over the second surface of the at least one membrane so that the acid gas other than carbon dioxide can pass through the membrane into the fluid and carbon dioxide from the fluid can pass from the liquid through the membrane and into the sweep gas.

In a number of embodiments, the fluid is a blood fluid (for example, whole blood or a component of blood such as blood plasma etc.) In a number of embodiments, the membrane includes immobilized carbonic anhydrase on or in the vicinity of the first surface thereof such that the immobilized carbonic anhydrase comes into contact with the fluid.

In still a further aspect, a respiratory assist device or a respiratory assist system for removal of at least a portion of carbon dioxide from a blood fluid hereof includes a plurality of hollow fiber membranes. Each of the plurality of hollow fiber membrane includes a first or inner surface and a second or outer surface. Each of the plurality of hollow fiber membranes is adapted to pass carbon dioxide, oxygen and at least one acid gas other than carbon dioxide therethrough. Each of the plurality of hollow fiber membranes is further adapted to limit or prevent passage of the blood fluid therethrough. The device and/or system further includes a sweep gas including the acid gas other than carbon dioxide and oxygen. The sweep gas is passed through each of the plurality of hollow fiber membranes so that the acid gas other than carbon dioxide and oxygen can pass through each of the plurality of hollow fiber membranes into the blood fluid, and carbon dioxide from the blood fluid can pass from the liquid through each of the plurality of hollow fiber membranes and into the sweep gas. Each of the plurality of hollow fiber membranes may, for example, include immobilized carbonic anhydrase on or in the vicinity of the first surface thereof such that the immobilized carbonic anhydrase comes into contact with the blood fluid.

DETAILED DESCRIPTION

It will be readily understood that the components of the embodiments, as generally described and illustrated in the figures herein, may be arranged and designed in a wide variety of different configurations in addition to the described exemplary embodiments. Thus, the following more detailed description of the exemplary embodiments, as represented in the figures, is not intended to limit the scope of the embodiments, as claimed, but is merely representative of exemplary embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

As used herein and in the appended claims, the singular forms "a," "an", and "the" include plural references unless the context clearly dictates otherwise. Thus, for example, reference to "an acid gas" includes a plurality of such acid gases and equivalents thereof known to those skilled in the art, and so forth, and reference to "the acid gas" is a reference to one or more such acid gasses and equivalents thereof known to those skilled in the art, and so forth.

Carbon dioxide is present in blood in three primary forms: $CO_2$ (dissolved), bicarbonate ($HCO_3^-$), or carbamate. As known in the chemical arts, $CO_2$ is interconvertible among these forms and the various forms can be in equilibrium with each other as described by a $CO_2$ dissociation curve. Most of the $CO_2$ in blood, however, exists in the form of $HCO_3^-$ in plasma and in red blood cells. In that regard, approximately 94% of plasma $CO_2$ and 82% of red blood cell $CO_2$ is in the form of $HCO_3^-$. The two species are interconvertible via the reaction:

The $CO_2$ generates via metabolic pathways in tissue and diffuses into red blood cells (RBCs), where it is hydrated into $HCO_3^-$ and hydrogen ions ($H^+$) by intracellular carbonic anhydrase (CA). The hydrogen ions formed are bound to hemoglobin while $HCO_3^-$ is diffused into plasma. However, very little $CO_2$ is hydrated in plasma because of a lack of CA in plasma. In lungs, the reaction is reversed. $HCO_3^-$ is converted into $CO_2$ via CA in red blood cells, and then exhaled. Some CA exists in lung tissue.

Carbonic anhydrase or CA (EC 4.2.1.1; MW 30,000 Da) is a metalloenzyme with a single zinc atom, which can effectively catalyze the reversible hydration and dehydration reaction of $CO_2$ ($CO_2+H_2O \leftrightarrows H^+ + HCO_3^-$). An assay for carbonic anhydrase activity and reactions that produce radiolabeled gases or small uncharged molecules. The enzyme enhances both hydration and dehydration rates over $10^5$-fold compared to reaction rates in the absence of CA, even though it is variable and depends on isoforms. Once again, CA is usually found within RBCs and lung tissue (alveolar epithelium).

In the present methods, devices and/or systems, carbon dioxide is removed from an aqueous fluid (for example, a blood fluid) through a membrane via a sweep gas. The sweep gas is used as a source to introduce acid into blood. Without limitation to any mechanism, unlike bulk addition of acid to blood, only the microenvironment surrounding the membrane (for example, a hollow fiber membrane or HFM) is significantly acidified, while the bulk blood properties remain substantially intact. In general, only the $CO_2$ pressure directly outside (that is, adjacent the first surface) of the membrane drives $CO_2$ removal.

The acid gas(es) in the present methods, devices and/or system may be introduced to the sweep gas from any sources and in any number of manners. For example, one or more acid gases may be directly infused into the seep gas from one or more gas tanks or reservoirs. Alternatively, a combination of gasses may be infused into the sweep gas, whereupon mixing under the appropriate conditions, results in creation of one or more acidic gases in the sweep gas. For example, nitric oxide and oxygen gas can react to create nitrogen dioxide, which forms nitric acid in an aqueous environment ($HNO_3$). Furthermore, various gasses may be combined such that, upon solvation in an aqueous environment, react to yield an acid. For example in an aqueous environment, nitric oxide can react with oxygen and water to form nitrous acid ($HNO_2$). In an alternative approach, one could evaporate liquid acid into its vapor form as a means of introducing it to the sweep gas. Utilizing a vacuum pump one could pull the vapor of an acid from its liquid form and introduce it to the sweep gas. Finally, one could pass the sweep gas through a cartridge containing a material which is able to elute an acidic product into the sweep gas stream.

In studies of bulk acidification of blood to increase $CO_2$ removal wherein an acid (for example, lactic acid) is infused directly into bulk blood, acidification requires a much greater amount of acid than required in the methods, devices and/or system hereof. Moreover, in bulk acidification, a deacidification stage may be required to remove the acid load infused into the blood. Although bulk blood acidification increases $CO_2$ removal, $ECCO_2R$ devices including bulk acid infusion are unable support the resting adult metabolic $CO_2$ production.

CA-immobilized bioactive hollow fiber membranes (HFMs) which convert bicarbonate to $CO_2$ directly at the HFM surface, accelerate $CO_2$ removal rates from blood in gas exchange devices. See, for example, U.S. Pat. No. 7,763,097, U.S. Pat. No. 8,043,411, U.S. Patent Application Publication No. 2012/0040429 and U.S. Patent Application Publication No. 2010/0331767, the disclosure of which are incorporated herein by reference. However, even with such bioactive coatings, current $ECCO_2R$ devices may be unable support the resting adult metabolic $CO_2$ production. The present inventors have discovered that the combined/synergistic effect of including an acid gas in the sweep gas and including immobilized carbonic anhydrase on or in the vicinity of the first surface of the membrane in removing $CO_2$ is much greater than use of either an acid gas in the sweep gas or immobilized CA alone.

Figure 1:
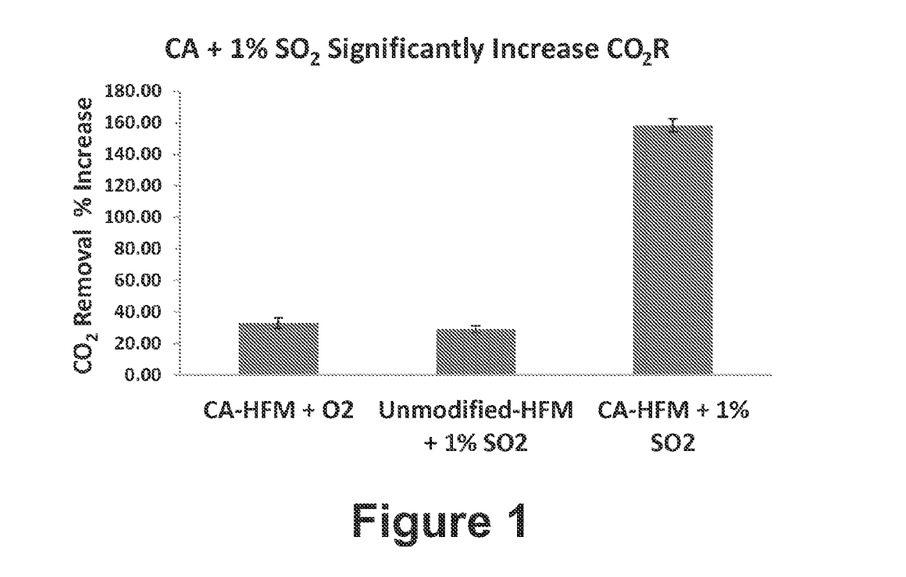
FIG. 1 illustrates a comparison of $CO_2$ removal for a system including carbonic anhydrase or CA immobilized upon a hollow fiber membranes (HFM) with an oxygen or $O_2$ sweep gas, a system including HFM without CA (unmodified HFM) and a sweep gas including $O_2$ and 1% (volume percent) $SO_2$ and a system including CA immobilized upon HFM and a sweep gas including $O_2$ and 1% $SO_2$.

In a number of representative studies hereof, hollow fiber membranes were used. FIG. 1 illustrates a comparison of $CO_2$ removal by a gas exchange device including HFM including immobilized CA with a sweep gas including only oxygen, a gas exchange device including unmodified HFM (that is, without immobilized CA) with a sweep gas including oxygen and 1% (volume) $SO_2$ and a gas exchange device including HFM with immobilized CA with a sweep gas including oxygen and 1% $SO_2$. As seen in FIG. 1, when employed independently the bioactive CA coating (CA-HFM) and dilute acidic sweep gas (Control-HFM+1% $SO_2$) increased $CO_2$ removal by 34% and 29% respectively. When both the bioactive CA coating and the dilute acidic sweep gas are employed jointly (CA-HFM+1% $SO_2$), a 149% increase in $CO_2$ removal is observed. These findings demonstrate dilute acidic sweep gas can increase $CO_2$ removal. When used in combination with bioactive CA-HFMs, dilute acidic sweep gas provides a synergistic effect which significantly increases $CO_2$ removal, while maintaining physiologic pH as discussed further below.

A mass flow controller may, for example, be used to control the amount of acid gas in the sweep gas. Percentages of acid gas provided herein are provided as volume %. The volume percentage range for acidic gases varies for each acid gas based upon its acidity and solubility. Once skilled in the art may readily determine a suitable range of volume % for a particular acid gas (considering, for example, acidity, solubility, biocompatibility of the acid gas and/or byproducts, and/or effectiveness in facilitating removal of $CO_2$). For $SO_2$ a range of 0-2% may, for example, be used. In a number of embodiments, the volume % of $SO_2$ in the sweep gas is no more than 1%. In a number of embodiments, the volume % of $SO_2$ is in the range of 0.5 to 1%.

Figure 2A:
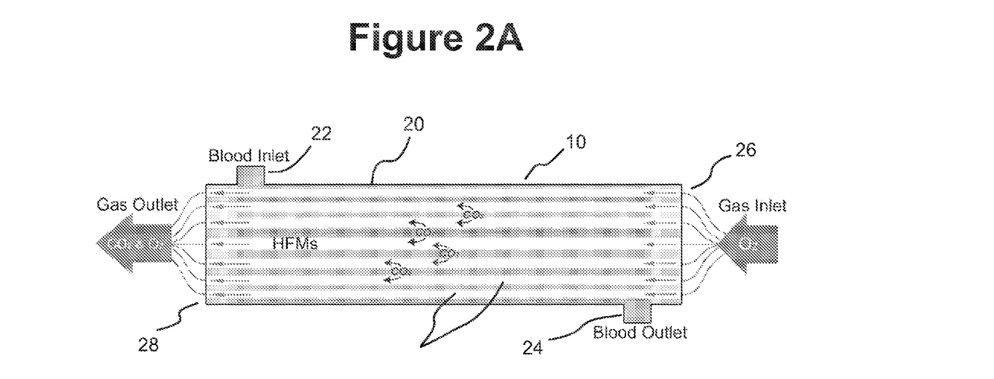
FIG. 2A illustrates a schematic diagram of an embodiment of a test device or a respiratory assist device hereof used for measuring $CO_2$ removal rates.
Figure 2B:
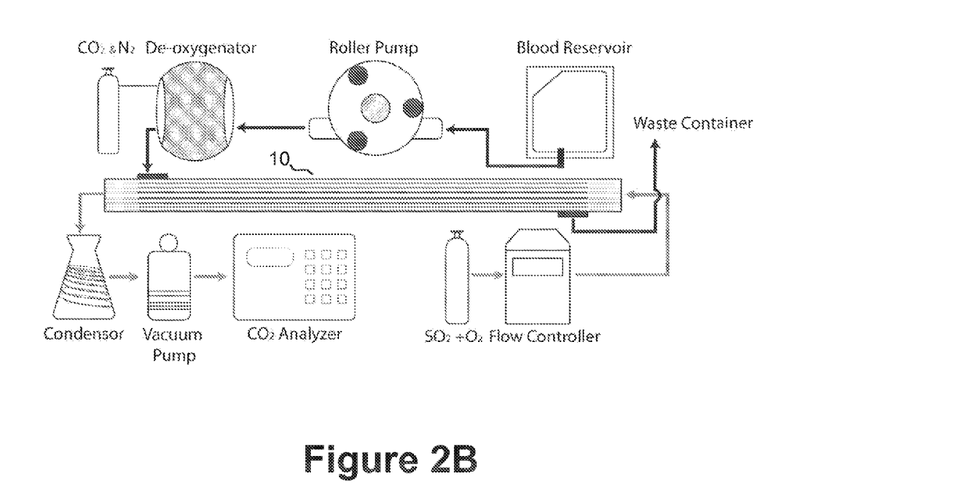
FIG. 2B illustrates an embodiment of an experimental system used in in vitro $CO_2$ gas exchange assessments hereof.

FIG. 2A illustrates a schematic diagram of an embodiment of a test system 10 (for example, a respiratory assist device) hereof used for measuring $CO_2$ removal rates of unmodified and CA-modified HFMs. In the studies hereof, bovine blood (introduced via an inlet 22 in a housing 20) was perfused over the outside of fibers 30 while oxygen sweep gas was passed through the fiber lumens in the opposite direction. Sweep gas was introduced via a gas inlet 26 and exited system 10 via a gas outlet 28. Blood exited system 10 via a gas outlet 24. FIG. 2B illustrates an embodiment of an experimental system used in the in vitro $CO_2$ gas exchange assessments hereof Both the blood reservoir and the de-oxygenator included a heat exchanger in operative connection therewith to maintain blood temperature at 37° C. Sweep gas including oxygen and one or more gases (delivered from one or more gas sources such as one or more pressurized tanks) that increase $H^+$ concentration in the liquid boundary layer adjacent HFMs 30 were introduced via gas inlet 26.

Figure 3A:
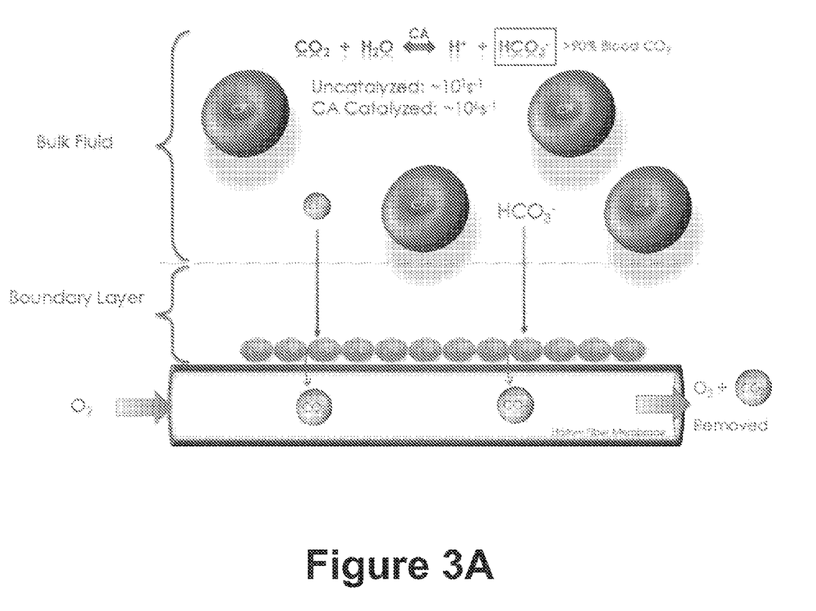
FIG. 3A illustrates schematically the removal of $CO_2$ via a hollow fiber membrane including immobilized CA with an $O_2$ sweep gas.
Figure 3B:
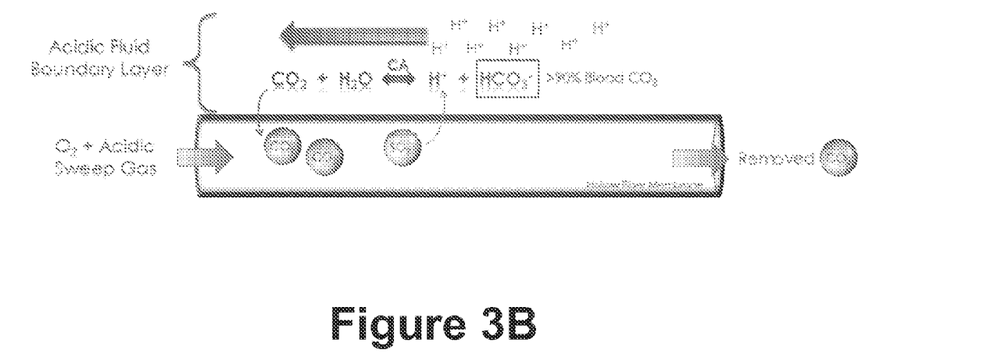
FIG. 3B illustrates schematically the introduction of dilute acidic gas into sweep gas stream to increase $H^+$ concentration in a liquid boundary layer adjacent the hollow fiber membrane to shift equilibrium to increase $CO_2$ catalysis.

The studies hereof demonstrated that dilute sulfur dioxide (1% $SO_2$) and other acid gases in an oxygen sweep gas can further increase $CO_2$ removal rates by, for example, creating an acidic microenvironment at the HFM surface, facilitating dehydration of bicarbonate to $CO_2$, while maintaining bulk blood pH in physiologic range. In addition to $SO_2$, $NO_2$ and HCl acid gases were also found to increase $CO_2$ removal rates. $NO_2$ required relatively high volume % (for example, approximately 20%) to significantly increase $CO_2$ removal rates. As illustrated schematically in FIGS. 3A and 3B, introduction of dilute acidic gas into sweep gas stream may increase $H^+$ concentration in liquid boundary layer and shift equilibrium to increase $CO_2$ catalysis. In general, "acid gases" are gases or combinations of gases in the sweep gases hereof that increase $H^+$ concentration in the liquid boundary layer adjacent membranes (for example, HFMs) hereof Without limitation to any mechanism, catalytic enhancement of bicarbonate dehydration to $CO_2$ may occur in the acidic microenvironment by a carbonic anhydrase coating. As a result of this coating, the acidic microenvironment created by the acidic sweep gas may result in faster conversion of bicarbonate to $CO_2$, significantly enhancing the effect of the acidic microenvironment around the membrane (for example, a hollow fiber membrane).

Table 1 sets forth a comparison of bulk blood acidification studies in the literature (wherein lactic acid is added to bulk blood) with studies hereof using $SO_2$ in an $O_2$ sweep gas within CA-modified HFM. For the lactic acid infusion studies, with no acid infusion, there is a 0% increase in $CO_2$ removal, and blood pH is normal at 7.39. At the highest lactic acid infusion rate, pH drops to 6.91, and $CO_2$ removal increases by 70%. In comparison, the $SO_2$ acid gas infusion from the HFM achieves better $CO_2$ removal enhancement with a 99% increase in $CO_2$ removal while decreasing pH only to 7.31. Further increase in $SO_2$ sweep gas concentration can yield up to a 168% increase in $CO_2$ removal, while decreasing pH only to 7.05. The concentration of sulfite in the fluid exiting the test system of the present studies was measured. The effective acid infusion rates set forth in Table 1 were calculated by multiplying the concentration of the acid product by the flow rate of blood through the device. The acid infusion rate to the body equals the acid concentration multiplied by the fluid flow rate. The acidic sweep gas was tested in a system using a flow rate of 45 mL/min. To compare the acid infusion rates to the bulk acid infusion rate using lactic acid, we multiplied the acid concentration thereof by the flow rate used in those studies (500 mL/min) In this manner, the effective acid infusion rates are directly comparable. The data for bulk lactic acid infusion set forth in Table 1 is found in Zanella, Alberto, et al., "Blood Acidification Enhances Carbon Dioxide Removal of Membrane Lung: An Experimental Study." *Intensive Care Medicine* 35, no. 8 (2009): 1484-1487. doi:10.1007/s00134-009-1513-5.)

TABLE 1

| | | | | | |
|---|---|---|---|---|---|
| Bulk Lactic Acid addition | Acid Infusion Rate (mmol/min) | 0 | 1 | 2 | 5 |
| | pH | 7.39 | 7.30 | 7.20 | 6.91 |
| | $CO_2$ Removal % Increase | 0 | 11 | 23 | 70 |
| CA-HFM + $SO_2$ | Acid Infusion Rate (mmol/min) | 0 | 0.24 | 1.27 | 3.99 |
| | pH | 7.40 | 7.31 | 7.21 | 7.05 |
| | $CO_2$ Removal % Increase | 34 | 99 | 148 | 168 |

Figure 4:
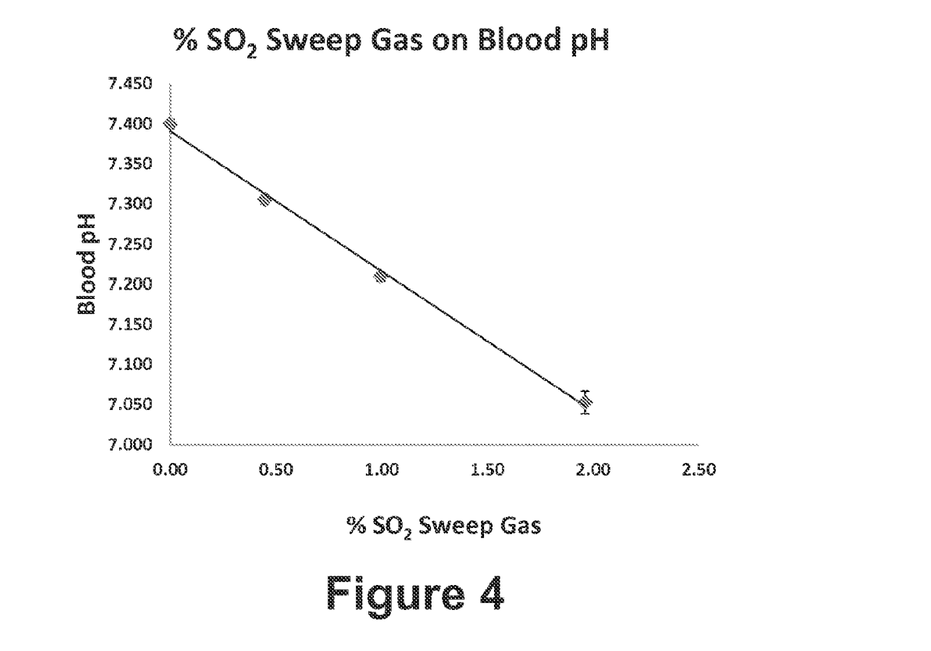
FIG. 4 illustrates the effect of the concentration of $SO_2$ in the sweep gas on blood pH.
Figure 5:
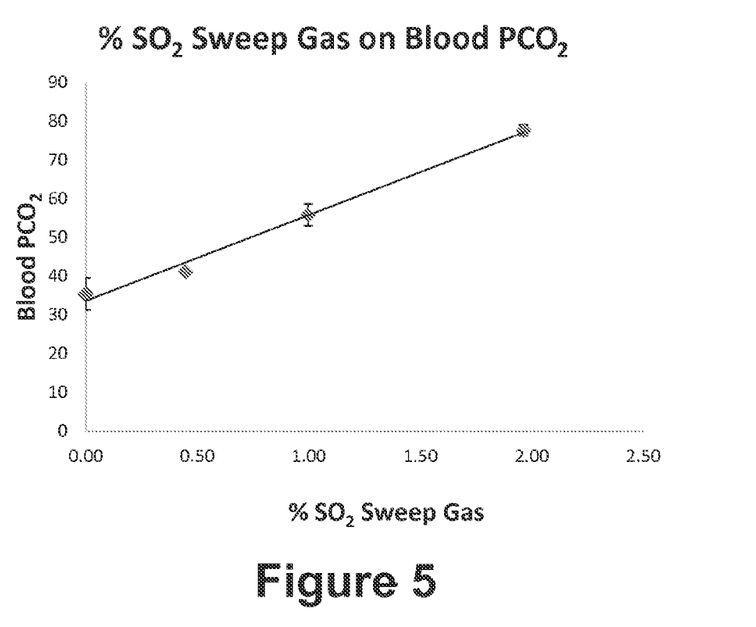
FIG. 5 illustrates the effect of the concentration of $SO_2$ in the sweep gas on $pCO_2$.
Figure 6:
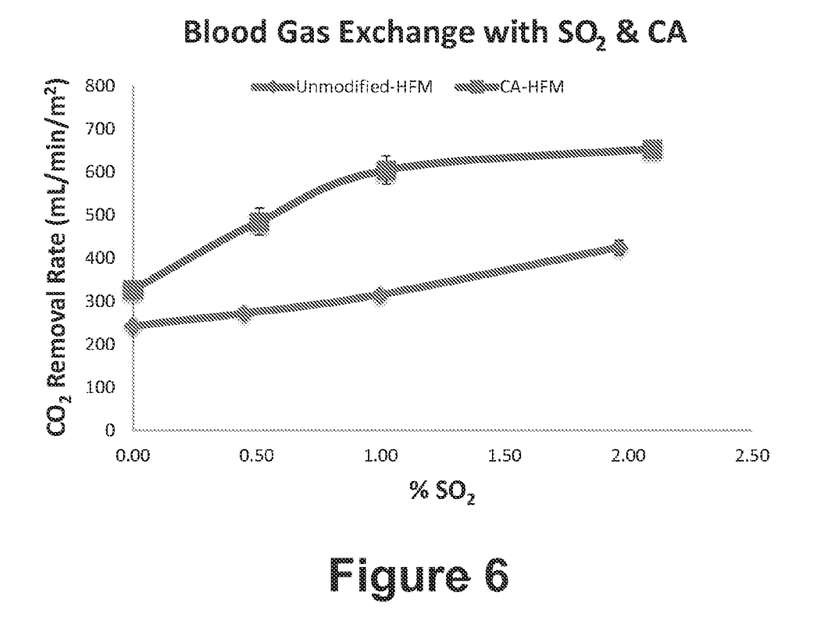
FIG. 6 illustrates the effect of the concentration of $SO_2$ in the sweep gas on $CO_2$ removal rate for unmodified HFM and HFM modified with immobilized CA.
Figure 7A:
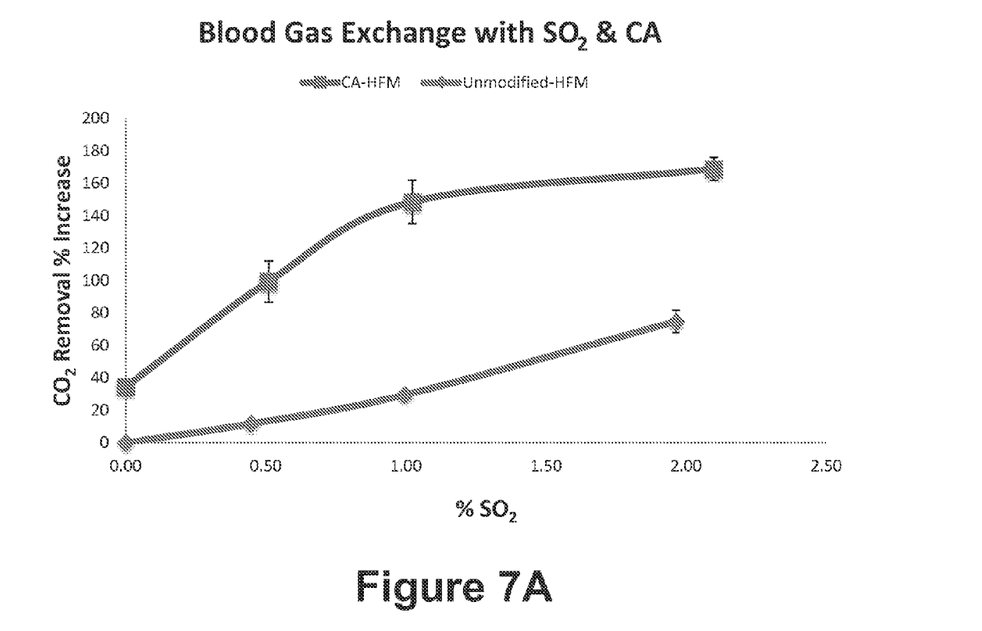
FIG. 7A illustrates the effect of the concentration of $SO_2$ in the sweep gas upon the percent increase in $CO_2$ removal for unmodified HFM and HFM modified with immobilized CA.
Figure 7B:
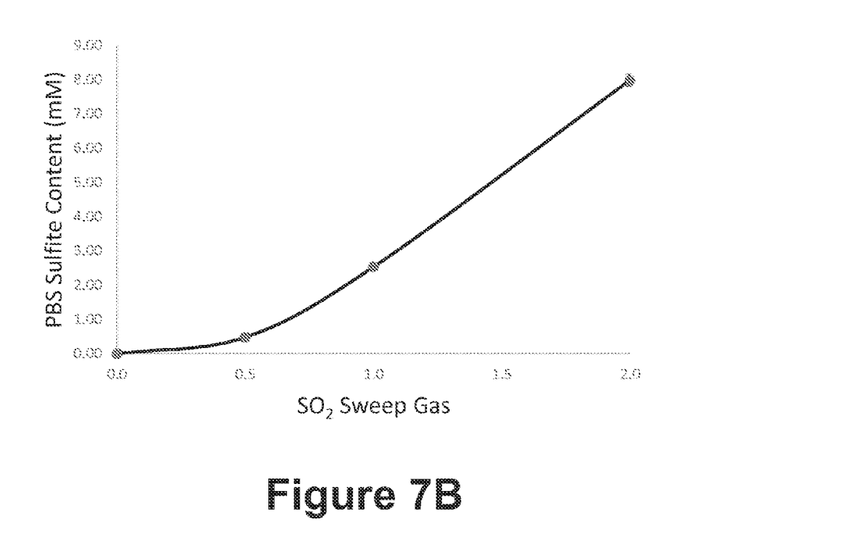
FIG. 7B illustrates the effect of the concentration of $SO_2$ within an oxygen sweep gas upon the sulfite concentration in the fluid exiting the device.

FIG. 4 illustrates a study of the change in blood pH with increasing $SO_2$ concentration (volume %) in the $O_2$ sweep gas. FIG. 5 sets forth the results of studies demonstrating that increasing the concentration $SO_2$ within the $O_2$ sweep gas increases the bulk blood $pCO_2$ leaving the device over the range of concentrations studied. FIG. 6 sets forth the results of studies demonstrating that increasing the concentration of $SO_2$ within the $O_2$ sweep gas significantly increases $CO_2$ removal rate using both CA-modified HFMs and unmodified HFMs. However, the increase is substantially larger in the case of CA-modified HFMs. FIG. 7A sets forth the results of studies demonstrating that increasing the concentration of $SO_2$ within the $O_2$ sweep gas significantly increases percent $CO_2$ removal using both CA-modified HFMs and unmodified HFMs. Once again, the increase is substantially larger in the case of CA-modified HFMs. FIG. 7B illustrates that increasing the concentration of $SO_2$ within an oxygen sweep gas increases the sulfite concentration in the fluid exiting the device.

As described, for example, in U.S. Pat. No. 7,763,097, in a number of embodiments, the membranes hereof (for example, HFM) include or are formed of a polymeric material. The polymeric material may be microporous or permeable such that $CO_2$ and the at least one acid gas other than $CO_2$ can pass/transport therethrough. The polymeric material may, for example, be microporous and sufficiently hydrophobic so that its pores remain gas filled after contacting blood or other aqueous fluids. The polymeric material may, for example, be an olefinic polymeric material. In a number of embodiments, the membrane includes a porous or microporous layer (for example, a first polymeric layer) and a gas permeable, nonporous layer adjacent the porous layer (for example, a second polymeric layer). A permeable, nonporous polymeric layer may, for example, include $CO_2$-permeable silicone (a polymerized siloxane or polysiloxane). Entities to improve hemocompatibility (for example, heparin) may be included in the first or blood contacting surface of the membrane.

Carbonic anhydrase may, for example, be immobilized on the membrane via adsorption, covalent bonding, ionic bonding or chelation. Free carbonic anhydrase may also be contacted with the fluid. In a number of embodiments, CA is covalently attached to first surface the membrane. Carbonic anhydrase may, for example, be covalently attached to the permeable, nonporous polymeric layer on an exterior surface of a microporous polymeric membrane (for example, an HFM) either directly or via a spacer group. Multiple layers of immobilized CA may also be provided, for example, by linking CA to itself in a multi-layer fashion.

Figure 8A:
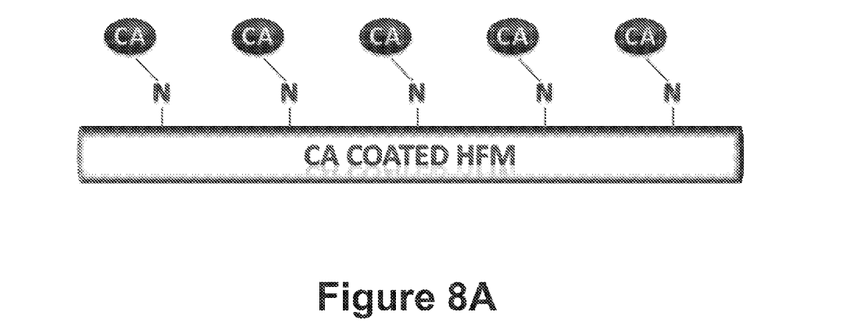
FIG. 8A illustrates covalent attachment of CA directly to a permeable and nonporous aminated siloxane layer of an HFM.
Figure 8B:
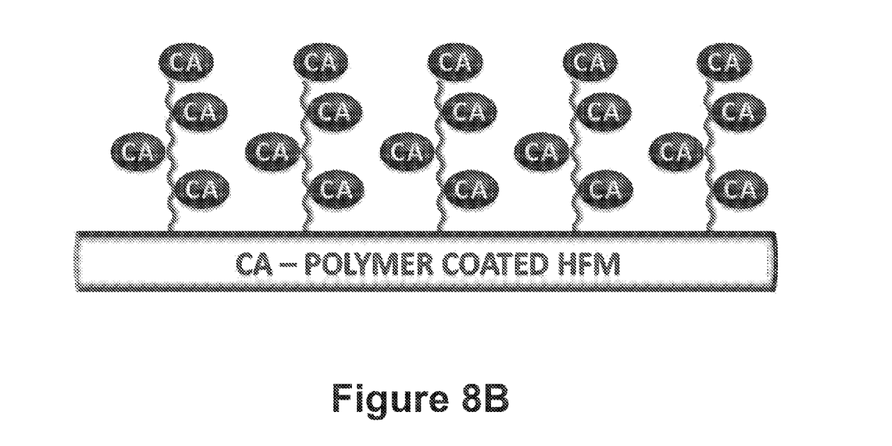
FIG. 8B illustrates covalent attachment of CA to a permeable and nonporous aminated siloxane layer of an HFM via a polymer spacer group.

Spacer groups such as polymeric spacer groups are often used to tether biomolecules to artificial surfaces. Such polymers can amplify the density of reactive functional groups for covalent immobilization of the biomolecule, and reduce steric hindrance between neighboring immobilized molecules and the artificial surface. FIG. 8A illustrates covalent attachment of CA directly to a permeable and nonporous siloxane and/or heparin layer of an HFM. Heparin was not used in the studied embodiments. FIG. 8B illustrates covalent attachment of CA to a permeable and nonporous siloxane and/or heparin layer of an HFM via a polymer spacer group. In a number of studies hereof, chitosan (a linear polysaccharide composed of randomly distributed β-(1-4)-linked D-glucosamine (deacetylated unit) and N-acetyl-D-glucosamine (acetylated unit)) was used as a polymeric spacer to tether CA to the surface of hollow fiber membranes. Glutaraldehye was used to link amine groups on the chitosan polymer to amine groups on the HFM surface. After washing unbound chitosan, a second glutaraldehyde step is used to link free amine groups on the immobilized chitosan polymer to amine groups on the CA molecule. A significant increase in immobilized CA enzyme activity on the fiber surface was demonstrated through the use of chitosan tethering. The chitosan/CA coating was used for all gas exchange testing. CA was also immobilized with alginate and hyaluronic polymers as spacers.

The first surface of the membrane may, for example, exhibit carbonic anhydrase activity of at least 20% of maximum theoretical activity of the first surface of the membrane based on monolayer surface coverage of carbonic anhydrase in the case that the carbonic anhydrase is immobilize on the first surface. In several embodiments, the first surface exhibits carbonic anhydrase activity of at least 40% of maximum theoretical activity of the fibers based on monolayer surface coverage of carbonic anhydrase. Further, the first surface may exhibit carbonic anhydrase activity of at least 60% of maximum theoretical activity of the first surface of the membranes based on monolayer surface coverage of carbonic anhydrase. Still further, the first surface may exhibit carbonic anhydrase activity of at least 80% or 100% of maximum theoretical activity of the first surface of the membrane based on monolayer surface coverage of carbonic anhydrase. Even higher activities are possible. Moreover, activities in excess of the maximum theoretical activity of the first surface of the membrane based on monolayer surface coverage of carbonic anhydrase in, for example, multilayered immobilization embodiments. In multilayerd embodiments, chemical chains including more than one carbonic anhydrase group are immobilized on the first surface.

EXPERIMENTAL

1. CA-Immobilized HFM

1A. Materials

TABLE 2

| Item | Item Description | Quantity |
| --- | --- | --- |
| Carbonic anhydrase | human CAII | 20 mL (20 mg) |
| Phosphate buffer (0.1M, pH 8.5) | Coupling buffer | 1 Liter |
| Alung Hemolung Hollow Fiber Membrane | 183 fibers/matt | 1 |
| Glutaraldehyde (5%, pH 8.5 .1M phosphate buffer) | Crosslinker in phosphate buffer | 40 mL |
| 1% Chitosan(w/v) in 1% (v/v) Acetic Acid | Spacer arm solution | 20 mL |
| Centripetal Mixer | | 1 |
| pH Meter (digital) | Thermo-Fisher | 1 |
| Pipettes and tips | Fisher | Various |
| 25 mL Corning glass tube | Glass tube with screw on cap | 3 |

1B. Sample Preparation.

HFM fiber mats were prepared by counting 186 fibers or 93 loops. One fiber was pulled from one end of the mat and two fibers from the other end.

A 100 mM Phosphate Buffer solution having a pH of 8.5 was prepared. As solution of 5% (v/v) glutaraldehyde or GA in 100 mM Phosphate Buffer (pH 8.5) was also prepared. A 1% Chitosan (w/v) solution in 1% (v/v) Acetic Acid was also prepared. Moreover, a solution of CA (1 mg/mL) was prepare in 100 mM Phosphate Buffer pH 8.5.

1C. Activation and Carbonic Anhydrase Immobilization.

Each mat was folded accordion style (as opposed to rolling) and place inside a tube (one mat per tube). 20 mL of 5% GA was added to each tube, and the tubes were rocked for 1 hour on a centripetal mixer (speed setting #10). This was followed by 10 minutes of rinsing with 100 mM Phosphate buffer pH 8.5 at speed 20 RPM. Rinsing for 10 minutes was repeated three times. 20 mL of 1% Chitosan was then added to each of the tubes, and the tubes were rocked for 1 hour on the centripetal mixer (speed setting #10). This was followed by 10 minutes of rinsing with 100 mM Phosphate buffer pH 8.5 at speed 20 RPM. Rinsing for 10 minutes was repeated three times. Subsequently, 20 mL of 5% GA was added to each of the tubes, and the tubes were rocked for 1 hour on the centripetal mixer (speed setting #10). This was followed by 10 minutes of rinsing with 100 mM Phosphate buffer pH 8.5 at speed 20 RPM. Rinsing for 10 minutes was repeated three times. 20 mL of CA solution was then added to each of the tubes, and the tubes were rocked overnight (approximately 12 hours) on the centripetal mixer (speed setting #10). This was followed by 20 minutes of rinsing with 100 mM Phosphate buffer pH 8.5 at speed 20 RPM. Rinsing for 20 minutes was repeated three times.

2. Gas Exchange Module and Testing System

A scaled-down model gas exchange module was fabricated by inserting the HFMs (183 fibers) into a ¼ in. ID polycarbonate-tubing (McMaster Carr, Elmhurst, Ill.) to which single luer locks were UV-glued 1.25 in. from each end in opposing directions. Both ends of the HFMs were secured to the tubing using an epoxy adhesive (Devcon, Danvers, Mass.) and then trimmed to the length of the tubing to expose the HFM lumens, yielding 6.9 cm of HFM uncovered within the module for a total active surface area of 0.0119 m². An in vitro recirculating test loop was used to assess $CO_2$ exchange rates using CA-immobilized and unmodified HFMs with $SO_2$ sweep gas.

The loop included a fluid reservoir, peristaltic pump, oxygenator, vacuum pump and the model gas exchange device. The testing fluid (1000 mL of Bovine Blood), flowed from a MasterFlex L/S peristaltic pump (Vernon Hills, Ill.) to a Terumo CAPIOX RX05 Baby RX Oxygenator (Ann Arbor, Mich.), then to the model gas exchange testing module and finally back to the reservoir. The inlet partial pressure of $CO_2$ ($PCO_2$) was adjusted to 50 mmHg and measured with a RAPIDLAB 248 Blood-Gas analyzer (Siemens, Deerfield, Ill.). Pure sulfur dioxide ($SO_2$) (and/or other gas(es) to increase acidity in the boundary layer outside the HFM) and pure oxygen gas was pulled by vacuum through two GR Series Gas Mass Flow Controllers (Fathom, Round Rock, Tex.), and mixed at a T connector to one central sweep gas line which flowed through the model gas exchange testing module HFM lumens, moisture trap condenser immersed in ice, KNF Lab UN811 KV.45P Vacuum Pump (USA) and finally a WMA-4 $CO_2$ Analyzer (PP Systems, Amesbury, Mass.). The concentration of $SO_2$ in the sweep gas was regulated by adjusting flow for oxygen and $SO_2$ through their respective mass flow controllers. The fluid flow rate through the module was set at 45 mL/min and the sweep gas through the HFM lumens was adjusted such that the $CO_2$ in the sweep gas exiting the device was constant at 3000 ppm. The fluid temperature was maintained at 37° C. by heat bath. The rate of $CO_2$ removal ($VCO_2$) for each model oxygenator device was calculated using the sweep gas flow rate ($Q_{OUT}^{STP}$) and $CO_2$ fraction ($FCO_2$) exiting the model respiratory assist device and then normalized to 50 mmHg to correct for small deviations in the inlet $PCO_2$:

$$VCO_2 = Q_{OUT}^{STP} F_{CO_2} \frac{50}{FCO_2}$$

The foregoing description and accompanying drawings set forth a number of representative embodiments at the present time. Various modifications, additions and alternative designs will, of course, become apparent to those skilled in the art in light of the foregoing teachings without departing from the scope hereof, which is indicated by the following claims rather than by the foregoing description. All changes and variations that fall within the meaning and range of equivalency of the claims are to be embraced within their scope.

What is claimed is:

1. A method for removal of at least a portion of carbon dioxide from blood fluid, comprising: placing a first surface of at least one membrane through which carbon dioxide and at least one acid gas other than carbon dioxide can pass in fluid in contact with the fluid, passing a sweep gas including oxygen and the at least one acid gas other than carbon dioxide over a second surface of the at least one membrane so that the at least one acid gas other than carbon dioxide can pass through the at least one membrane into the fluid, and carbon dioxide from the aqueous fluid can pass from the liquid through the at least one membrane and into the sweep gas, the at least one membrane being adapted to limit or prevent passage of the fluid therethrough, wherein the concentration of the acid gas other than carbon dioxide in the sweep gas is sufficient to decrease pH in the boundary layer adjacent to the at least one membrane while maintaining bulk blood fluid pH within a physiological range, the at least one membrane comprising immobilized carbonic anhydrase on or in the vicinity of the first surface thereof such that the immobilized carbonic anhydrase comes into contact with the blood fluid, wherein the acid gas other than carbon dioxide and the carbonic anhydrase function synergistically in the removal of carbon dioxide.

2. The method of claim 1 wherein the fluid is blood.

3. The method of claim 1 wherein the carbonic anhydrase is immobilized on the first surface and the first surface exhibits a carbonic anhydrase activity of at least 20% of maximum theoretical activity of the first surface of the at least one membrane based on monolayer surface coverage of carbonic anhydrase surface.

4. The method of claim 1 wherein the carbonic anhydrase is immobilized on the first surface and the first surface exhibits a carbonic anhydrase activity of at least 40% of maximum theoretical activity of the first surface of the at least one membrane based on monolayer surface coverage of carbonic anhydrase.

5. The method of claim 1 wherein the carbonic anhydrase is immobilized on the first surface and the first surface exhibits a carbonic anhydrase activity of at least 60% of maximum theoretical activity of the first surface of the at least one membrane based on monolayer surface coverage of carbonic anhydrase.

6. The method of claim 1 wherein the carbonic anhydrase is immobilized on the first surface and the first surface exhibits a carbonic anhydrase activity of at least 80% of maximum theoretical activity of the first surface of the at least one membrane based on monolayer surface coverage of carbonic anhydrase.

7. The method of claim 1 wherein the carbonic anhydrase is immobilized on the first surface and the first surface exhibits a carbonic anhydrase activity which exceeds the maximum theoretical activity of the first surface of the at least one membrane based on monolayer surface coverage of carbonic anhydrase.

8. The method of claim 1 wherein the at least one membrane comprises a polymeric material.

9. The method of claim 8 wherein the carbonic anhydrase is immobilized on the at least one membrane via adsorption, covalent bonding, ionic bonding or chelation.

10. The method of claim 8 wherein the carbonic anhydrase is covalently attached to the polymeric material.

11. The method of claim 8 wherein the polymeric material is microporous or permeable such that $CO_2$ and the at least one acid gas other than $CO_2$ can pass therethrough.

12. The method of claim 11 wherein the polymeric material is microporous and sufficiently hydrophobic so that its pores remain gas filled after contacting the blood fluid.

13. The method of claim 12 wherein the polymeric material is an olefinic polymeric material.

14. The method of claim 11 wherein the carbonic anhydrase is covalently attached to the first surface of a microporous polymeric hollow fiber.

15. The method of claim 14 wherein the first surface is an outer surface of the microporous polymeric hollow fiber and an interior lumen of the microporous polymeric hollow fiber receive the sweep gas therethrough, the sweep gas further comprising oxygen and the microporous polymeric hollow fiber being adapted to pass oxygen and the at least one acid gas other than carbon dioxide into the blood fluid while carbon dioxide passes from the blood fluid to the interior lumen of the microporous polymeric hollow fiber.

16. The method of claim 15 wherein the carbonic anhydrase is covalently attached to a permeable, nonporous polymeric layer positioned on an exterior surface of the microporous polymeric hollow fiber.

17. The method of claim 16 wherein the permeable, nonporous polymeric layer comprises $CO_2$-permeable silicone.

18. The method of claim 15 wherein the at least one membrane comprises a plurality of membranes formed by a plurality of the microporous polymeric hollow fibers.

19. The method of claim 1 wherein the at least one membrane comprises a porous layer and a gas permeable, nonporous layer adjacent the porous layer.

20. The method of claim 1 further comprising contacting the blood fluid with free carbonic anhydrase.

21. The method of claim 1 wherein carbon dioxide is present in the fluid in the form of bicarbonate ion.

22. The method of claim 1 wherein the at least one acid gas other than $CO_2$ is sulfur dioxide, hydrogen sulfide, nitrogen dioxide, nitric oxide, or hydrogen iodide.

23. The method of claim 1 wherein the at least one acid gas other than $CO_2$ is sulfur dioxide or nitrogen dioxide.

24. The method of claim 1 wherein the at least one acid gas other than $CO_2$ is sulfur dioxide.

25. A system for removal of at least a portion of carbon dioxide from a blood
fluid blood, comprising: at least one
  membrane comprising a first surface and a second surface, the at least one membrane being adapted to pass carbon dioxide and at least one acid gas other than carbon dioxide from a sweep gas therethrough, the at least one membrane being further adapted to limit or prevent passage of the fluid therethrough, the at least one source of the sweep gas, adapted to be placed in fluid connection with the second surface of the at least one membrane to pass the sweep gas over the second surface of the at least one membrane so that the at least one acid gas other than carbon dioxide can pass through the at least one membrane into the fluid and carbon dioxide from the fluid can pass from the aqueous fluid through the at least one membrane and into the sweep gas, wherein the concentration of the acid gas other than carbon dioxide in the sweep gas is sufficient to decrease pH in the boundary layer adjacent to the at least one membrane while maintaining bulk blood pH in a physiological range, the at least one membrane comprising immobilized carbonic anhydrase on or in the vicinity of the first surface thereof such that the immobilized carbonic anhydrase comes into contact with the blood fluid, wherein the acid gas other than carbon dioxide and the carbonic anhydrase function synergistically in the removal of carbon dioxide.

26. The system of claim 25 wherein the fluid is blood.

27. A respiratory assist system for removal of at least a portion of carbon dioxide from a blood fluid, comprising: a plurality of hollow fiber membranes, each of the plurality of hollow fiber membrane comprising a first or inner surface and a second or outer surface, each of the plurality of hollow fiber membranes being adapted to pass carbon dioxide, oxygen and at least one acid gas other than carbon dioxide therethrough, each of the plurality of hollow fiber membranes being further adapted to limit or prevent passage of the blood fluid therethrough, and a source of a sweep gas in fluid connection with each of the plurality of hollow fiber membranes, the sweep gas comprising the at least one acid gas other than carbon dioxide and oxygen, the sweep gas is passed from the source of sweep gas and through each of the plurality of hollow fiber membranes so that the at least one acid gas other than carbon dioxide and oxygen can pass through each of the plurality of hollow fiber membranes into the blood fluid, and carbon dioxide from the blood fluid can pass from the blood fluid through each of the plurality of hollow fiber membranes and into the sweep gas, wherein the concentration of the acid gas other than carbon dioxide in the sweep gas is sufficient to decrease pH in the boundary layer adjacent to the at least one membrane while maintaining bulk blood fluid pH in a physiological range, each of the plurality of hollow fiber membranes comprising immobilized carbonic anhydrase on or in the vicinity of the first surface thereof such that the immobilized carbonic anhydrase comes into contact with the blood fluid, wherein the acid gas other than carbon dioxide and the carbonic anhydrase function synergistically in the removal of carbon dioxide.

28. The system of claim 27 wherein the carbonic anhydrase is covalently attached to a permeable, nonporous polymeric layer positioned on an exterior surface of each of the plurality of hollow fiber membranes which comprise a permeable, nonporous polymeric layer on the outer surface thereof.

29. The system of claim 28 wherein the permeable, nonporous polymeric layer comprises $CO_2$-permeable silicone.

* * * * *

UNITED STATES PATENT AND TRADEMARK OFFICE
CERTIFICATE OF CORRECTION

PATENT NO. : 9,814,821 B2
APPLICATION NO. : 14/405038
DATED : November 14, 2017
INVENTOR(S) : William J. Federspiel, David T. Arazawa and Jeremy D. Kimmel Page 1 of 1

It is certified that error appears in the above-identified patent and that said Letters Patent is hereby corrected as shown below:

In the Claims

Column 13, Claim 25, Line 31 after "fluid" delete "blood"

Signed and Sealed this
Twenty-third Day of January, 2018

Joseph Matal
*Performing the Functions and Duties of the*
*Under Secretary of Commerce for Intellectual Property and*
*Director of the United States Patent and Trademark Office*